(12) United States Patent
Fordham et al.

(10) Patent No.: US 8,680,858 B2
(45) Date of Patent: Mar. 25, 2014

(54) NMR LOGGING OF MISCIBLE DISPLACEMENT

(75) Inventors: Edmund Fordham, Kedington (GB); Denise Freed, Newton Highlands, MA (US); Yuesheng Cheng, Edmonton (CA); John Edwards, Medinat Al Alam (OM)

(73) Assignee: Schlumberger Technology Corporation, Sugar Land, TX (US)

( * ) Notice: Subject to any disclaimer, the term of this patent is extended or adjusted under 35 U.S.C. 154(b) by 360 days.

(21) Appl. No.: 13/002,415

(22) PCT Filed: Jun. 29, 2009

(86) PCT No.: PCT/IB2009/006095
§ 371 (c)(1),
(2), (4) Date: Feb. 22, 2011

(87) PCT Pub. No.: WO2010/004393
PCT Pub. Date: Jan. 14, 2010

(65) Prior Publication Data
US 2011/0175607 A1 Jul. 21, 2011

Related U.S. Application Data

(60) Provisional application No. 61/079,987, filed on Jul. 11, 2008.

(51) Int. Cl.
*G01V 3/32* (2006.01)
(52) U.S. Cl.
USPC ........................................................ 324/303

(58) Field of Classification Search
USPC .......... 324/300–322; 166/250.1, 250.02, 270, 166/313; 436/173–181
See application file for complete search history.

(56) References Cited

U.S. PATENT DOCUMENTS

| | | | |
|---|---|---|---|
| 4,800,957 A | | 1/1989 | Stevens, Jr. et al. |
| 4,941,533 A | * | 7/1990 | Buller et al. .................. 166/270 |
| 5,117,907 A | | 6/1992 | Hsu |
| 5,213,379 A | | 5/1993 | Taniguchi et al. |
| 5,214,384 A | | 5/1993 | Sprunt et al. |
| 5,486,762 A | | 1/1996 | Freedman et al. |
| 5,524,708 A | | 6/1996 | Isaacs |
| 5,696,448 A | | 12/1997 | Coates et al. |
| 5,796,252 A | | 8/1998 | Kleinberg et al. |
| 6,115,671 A | | 9/2000 | Fordham et al. |

(Continued)

FOREIGN PATENT DOCUMENTS

CA 2646770 6/2009

OTHER PUBLICATIONS

Fordham et al: "Partially restricted diffusion in a permeable sandstone: Observations by stimulated echo PFG NMR"; Magnetic resonance imaging yr:1994 vol. 12 iss:2 p. 279-284.

(Continued)

*Primary Examiner* — Melissa Koval
*Assistant Examiner* — Rishi Patel

(57) ABSTRACT

NMR logging in a wellbore is used to monitor an oil reservoir during oil recovery by miscible displacement. Diffusivity distributions found by NMR logging indicate whether one or two phases are present and composition of residual oil. Operation of the oil recovery procedure may be maintained or modified in response to monitoring of the reservoir.

19 Claims, 3 Drawing Sheets

(56) References Cited

U.S. PATENT DOCUMENTS

| | | | |
|---|---|---|---|
| 6,115,971 | A | 9/2000 | Loebertmann et al. |
| 6,140,818 | A | 10/2000 | Hurlimann |
| 6,279,658 | B1* | 8/2001 | Donovan et al. ............... 166/313 |
| 6,316,940 | B1 | 11/2001 | Akkurt |
| 6,570,382 | B1 | 5/2003 | Hurlimann et al. |
| 7,741,841 | B2 | 6/2010 | Edwards et al. |
| 2004/0008027 | A1 | 1/2004 | Prammer |
| 2004/0055745 | A1* | 3/2004 | Georgi et al. ............ 166/250.02 |
| 2004/0253473 | A1 | 12/2004 | Weekes et al. |
| 2004/0253743 | A1* | 12/2004 | Freed ............................ 436/173 |
| 2005/0104587 | A1 | 5/2005 | Akkurt |
| 2006/0122779 | A1 | 6/2006 | Minh et al. |
| 2008/0066904 | A1* | 3/2008 | Van Hal et al. ............ 166/250.1 |
| 2008/0206887 | A1* | 8/2008 | Chen et al. .................... 436/173 |
| 2009/0302852 | A1 | 12/2009 | Levesque et al. |

OTHER PUBLICATIONS

Freed et al: "Scaling Laws for Diffusion Coefficients in Mixtures of Alkanes"; Physical Review Letters vol. 94, 067602 (2005).

Freed, D E: "Dependence on chain length of NMR relaxation times in mixtures of alkanes"; J. Chem. Phys. 126, 174502 (2007).

Freedman et al: "Field Applications of a New Nuclear Magnetic Resonance Characterization method"; SPE Reservoir Evaluation and Engineering, Dec. 2002 pp. 455-462; SPE paper 81197.

Greiner-Schmidt et al: "Self-diffusion in the compressed fluid lower alkanes: Methane, ethane, and propane"; J. Chem. Phys. 94, 5643 (1991).

Hürlimann et al: "Diffusion-relaxation distribution functions of sedimentary rocks in different saturation states"; Magnetic Resonance Imaging 21 (3-4), pp. 305-310 (2003).

"Hürlimann et al:""Hydrocarbon Composition from NMR Diffusion and Relaxation Data""; SPWLA 49th Annual Logging Symposium, Paper U; May 25-28, 2008".

Hürlimann et al: "Quantitative Measurement of Two-Dimensional Distribution Functions of Diffusion and Relaxation in Grossly Inhomogeneous Fields"; Journal of Magnetic Resonance 157, 31-42 (2002).

Hürlimann et al: "Spin Dynamics of Carr—Purcell—Meiboom—Gill-like Sequences in Grossly Inhomogeneous B0 and B1 Fields and Application to NMR Well Logging"; Journal of Magnetic Resonance 143, 120-135 (2000).

"Hürlimann et al: ""The diffusion-spin relaxation time distribution function as an experimental probe to characterize fluid mixtures in porous media""Journal of Chemical Physics vol. 117, Issue 22, Dec. 8, 2002, pp. 10223-10232".

"Hürlimann, M D: ""Diffusion and Relaxation Effects in General Stray Field NMR Experiments""; Journal of Magnetic Resonance vol. 148, Issue 2, Feb. 2001, pp. 367-378".

Hürlimann, M D: "Diffusion-relaxation distribution functions of sedimentary rocks in different saturation states"; Magnetic Resonance Imaging yr:2003 vol. 21 iss:3-4 p. 305-310.

Kleinberg et al: "NMR properties of reservoir fluids"; The Log Analyst yr:1996 vol. 37 iss:6 p. 20-32.

Leu et al: "Fixed and pulsed gradient diffusion methods in low-field core analysis"; Magnetic resonance imaging yr:2005 vol. 23 (iss:2) p. 305-309.

Peled et al: "Water Diffusion, T2, and Compartmentation in Frog Sciatic Nerve"; Magnetic Resonance in Medicine 42:911-918 (1999) and erratum published at vol. 43 (4), pp. 620 (2000).

Venkataramanan et al: "Solving Fredholm integrals of the first kind with tensor product structure in 2 and 2.5 dimensions"; IEEE Transactions on Signal Processing yr:2002 vol. 50 iss:5 p. 1017-1026.

Seland et al: "Combining PFG and CPMG NMR Measurements for Separate Characterization of Oil and Water Simultaneously Present in a Heterogeneous System"; Appl. Magn. Reson. 24, 41-53 (2003).

Search Report and Written Opinion PCT/IB2009/006905; Mar. 22, 2010.

Heaton et al., "SPE 77400: Applications of a New-Generation NMR Wireline Logging Tool," SPE International, 2002: pp. 1-10.

Lo et al., "SPE 63217: Correlations of NMR Relaxation Time with Viscosity, Diffusivity, and Gas/Oil Ratio of Methane/ Hydrocarbon Mixtures," SPE International, 2000: pp. 1-15.

* cited by examiner

NMR LOGGING OF MISCIBLE DISPLACEMENT

FIELD OF THE INVENTION

This invention is concerned with monitoring and predicting changes which take place in an oil reservoir during enhanced oil recovery with a miscible drive fluid, a procedure which is also known as miscible displacement.

BACKGROUND OF THE INVENTION

Miscible displacement is a form of enhanced oil recovery in which a fluid which is partially miscible with oil is injected into the oil reservoir. Fluids used for this purpose may be gaseous at ambient temperature and pressure but volatile hydrocarbons and supercritical gas have also been used. Examples of fluids which have been used as drive fluids include methane, liquefied petroleum gas such as propane, and carbon dioxide (which may or may not be in a supercritical state at reservoir temperature and pressure). The fluids are termed 'miscible' because they can dissolve in the oil but they are usually not miscible with oil in all proportions. When the miscible drive fluid is injected into a reservoir, it initially dissolves in the oil leading to a diluted oil phase with reduced viscosity. Dissolution of the drive fluid can progress until the oil becomes saturated with the fluid. At the same time some constituents of the oil, generally its more volatile constituents, can dissolve in the drive fluid until the fluid becomes saturated with these. The eventual result, if equilibrium is reached, is two-phase mixture of
  (i) oil that has become saturated with dissolved drive fluid and
  (ii) drive fluid saturated with oil constituents.

During such a miscible displacement operation, drive fluid is injected into the formation through one or more injection wells and moves through the reservoir towards one or more production wells. The region where injected fluid meets undiluted original oil is a 'flood front' which is typically less than one meter thick. Within this flood front the drive fluid dissolves in the oil until the oil becomes saturated. Behind the flood front there is a free gas phase together with residual oil which is saturated with drive fluid and somewhat depleted of the more volatile constituents of the original oil. This residual oil will be moving more slowly than the drive fluid and flood front. Indeed the residual oil may not be moving within the reservoir at all.

When planning the extraction of oil from a reservoir (whether, or not an enhanced recovery technique is contemplated) it is normal practice to determine the properties of the reservoir—including its pressure and temperature and the composition of the oil in it—and then seek to predict what changes will take place during the course of the recovery operation, with a view to achieving maximum economic recovery of oil. An extraction plan is likely to involve a number of design choices, including the composition of the drive fluid. Capital investment in an enhanced oil recovery operation may be very substantial—high cost of surface processing facilities, for instance. Consequently it may be desirable to monitor progress and changes within the reservoir, to check that the operation is proceeding as predicted, and take remedial action if required—such as by modifying one or more of the original design choices. Possibilities would include changes to the drive fluid composition and/or changes to the relative rates of injection of drive fluid through each of a plurality of injection wells. One parameter of considerable economic importance is the composition of the residual oil which is not recovered.

Techniques for monitoring during miscible displacement include the use of observation wells located intermediately between production wells and injection wells for putting the drive fluid into the reservoir. Nuclear magnetic resonance (NMR) has been used in well logging for a number of years. There are a number of published techniques for obtaining and interpreting NMR data but so-called two dimensional NMR has become well established. A method for obtaining such data is described in U.S. Pat. No. 6,570,382 and a wireline tool for NMR logging is described in U.S. Pat. No. 6,140,818. Both of these documents are incorporated herein by reference. An NMR logging tool which is currently in use is the Schlumberger MR scanner.

Two-dimensional NMR measurements provide a map of diffusion coefficients against spin-spin relaxation time, usually referred to as $T_2$ relaxation time. The coordinates for each point on the map are values of diffusion coefficient and $T_2$ relaxation time and the map shows the concentration of molecules (or proportion of the composition) displaying that combination of the diffusion coefficient and $T_2$ relaxation time. The information given by such a map can be projected as a graph of concentration plotted against relaxation time and also as a graph of concentration plotted against diffusion coefficient. The latter plot, i.e. of concentration against diffusion coefficient, is referred to as a diffusivity distribution. The technique of obtaining such a map has been described in U.S. Pat. No. 6,570,382 in which FIG. 7 shows a map and the two projections.

It has been shown that diffusion coefficients and $T_2$ relaxation times of mixtures of alkanes follow simple scaling laws based on the chain length of the constituents and the mean chain length of the mixture. These scaling laws can be used to calculate chain lengths in a mixture from the distribution of the diffusion coefficients and also to calculate the viscosity of a mixture. Compositions calculated from NMR data are in good agreement with compositions determined by laboratory analysis. See US published application 2004/0253743, also Freed, Burcaw and Song: "Scaling Laws for Diffusion Coefficients in Mixtures of Alkanes" Physical Review Letters Vol 94, 067602 (2005), Freed: "The dependence on chain length of NMR relaxation times in mixtures of alkanes, J. Chem. Phys. Vol 126, 174502 (2007), and Hürlimann, Freed, Zielinski, Song, Leu, Straley, Cao Minh, and Boyd: "Hydrocarbon composition from NMR diffusion and relaxation data" SPWLA 49th Annual Logging Symposium, May 2008, Paper U. These documents are incorporated herein by reference.

Thus it is possible to infer hydrocarbon fluid composition and viscosity from NMR determinations of diffusion coefficients and $T_2$ relaxation times obtained by NMR logging.

Tools for predicting changes during the course of extraction from a reservoir include a number of proprietary computer programs. For example PVTPro available from Schlumberger is an equation-of-state based program able to predict fluid properties and phase behaviour of a given hydrocarbon composition under various conditions of temperature and pressure. Simulator programs set up a computer model of an oil reservoir and can be used to predict displacement of fluid and composition changes within the reservoir during the course of oil recovery.

It is not unusual to make adjustments to a computer simulation or a predictive program, for example by adjusting the equation of state which is used, so as to arrive at a better fit to observed data. The hope is that such adjustments will give improvements in future predictions for the individual reservoir concerned, although the changes made may be empirical rather than evidence-based.

SUMMARY OF THE INVENTION

We have now recognised that diffusivity distribution can be a useful indicator, not only of composition but also of the phases present. We have found that the diffusivity distributions of:

oil saturated with drive fluid,
drive fluid saturated with components of oil and
a two phase mixture of them both are distinctively different from each other and from diffusivity distributions of undiluted oil and oil which contains dissolved drive fluid but which is not saturated with it. This enhances the versatility of NMR logging.

In a first aspect, this invention provides a method of observing composition in a region of an oil reservoir during displacement with a drive fluid which is partially miscible with the oil in the reservoir, by locating an NMR logging tool within a wellbore penetrating the reservoir and operating the tool to measure a diffusivity distribution of the composition in the vicinity of the wellbore, and deriving properties of composition or phase, or changes in composition or phase of the oil in the vicinity of the wellbore from the measured diffusivity distribution. The method may comprise communicating measurements from the logging tool at least on computer or electronic processor and using at least one processor to perform the step of deriving properties or changes in properties.

This method of observing composition during displacement will of course form part of an overall process of extracting oil from a reservoir by displacement with a drive fluid.

It is particularly envisaged that this method of observing composition will be used to monitor changes in an oil reservoir over a period of time as enhanced oil recovery takes place. Consequently, logging with an NMR logging tool may be carried out at intervals so that diffusivity distributions at different times can be compared with each other to show changes which have taken place in the vicinity of the wellbore. As will be explained in more detail below, it is possible to detect the passing flood front by observing a change in the NMR log, and also to go further and obtain information about composition after the flood front has passed.

Logging may be carried out in a plurality of wellbores penetrating the reservoir, to monitor what is happening in different regions of the reservoir. These wellbores may be observation wells drilled for the purpose of monitoring changes during miscible displacement or may be wells initially drilled for some other purpose, eg as exploratory wells. Since the wellbores which penetrate the reservoir will be in place during production from the reservoir as oil recovery takes place, they will need to be cased bores. NMR has typically been confined to open holes because magnetic field cannot penetrate a steel casing. However, it can be used in cased boreholes provided a non-magnetic casing is used for the portion of the wellbore which penetrates the reservoir, for instance a fibre-reinforced plastic casing.

Drive fluid which is used for recovery may be any of the fluids which are normally used. One possibility is natural gas, another is carbon dioxide. Mixtures of natural gas and carbon dioxide may be used. Natural gas may be classed as at least 75% by volume of a mixture of hydrocarbons which are gaseous at ambient temperature and pressure (25° C. and 1 bar) and probably at least 40% or at least 50% methane. A carbon dioxide based drive fluid may contain may contain at least 50% more likely at least 75% of the pure gas while a mixture containing carbon dioxide and natural gas may contain at least 75% by volume of gas which is either carbon dioxide or is hydrocarbon that is gaseous at 25° C. and 1 bar. Additives such as solvents (suggested in U.S. Pat. Nos. 4,800, 957 and 5,117,907 for instance) or surfactants may be included in a drive fluid to further enhance oil recovery, especially if it becomes a supercritical fluid downhole.

A further aspect of this invention relates to computer prediction based on equations of state. There are a number of published equations of state, useful to describe and predict the behaviour of individual compounds and compositions. They seek to account for the observable behaviour of real substances which do not obey the ideal gas laws. Whilst useful and effective, they are not perfect. In consequence any computer program using an equation of state to make a prediction of conditions does not always give an accurate prediction.

According to an aspect of this invention, a method of predicting number of phases and phase composition in an oil reservoir during recovery by miscible displacement, by computation from predetermined compositions and values of pressure and temperature, is characterised by constraining the computation to conform to phase and composition determinations derived from diffusivity distributions obtained by NMR logging.

In a further aspect of this invention, it is proposed that knowledge of the reservoir oil composition, pressure and temperature, together with a chosen drive fluid composition, is used to calculate diffusivity distributions and viscosities. This can be done using the formulae which the literature mentioned above uses for inferring compositions from diffusivity distributions. So, it is proposed that diffusivity distributions and viscosities calculated from the composition of the original oil in the reservoir and the composition of the drive fluid should be utilised in a computer simulation of the reservoir to predict the movement of oil and changes in composition during miscible displacement.

The output from a program such as PVTPro or a computer simulation of a reservoir will generally be displayed on a computer monitor or printed out on paper.

BRIEF DESCRIPTION OF THE DRAWINGS

The invention will now be further explained and exemplified with reference to embodiments illustrated by the following diagrammatic drawings in which.

DETAILED DESCRIPTION

Figure 1:
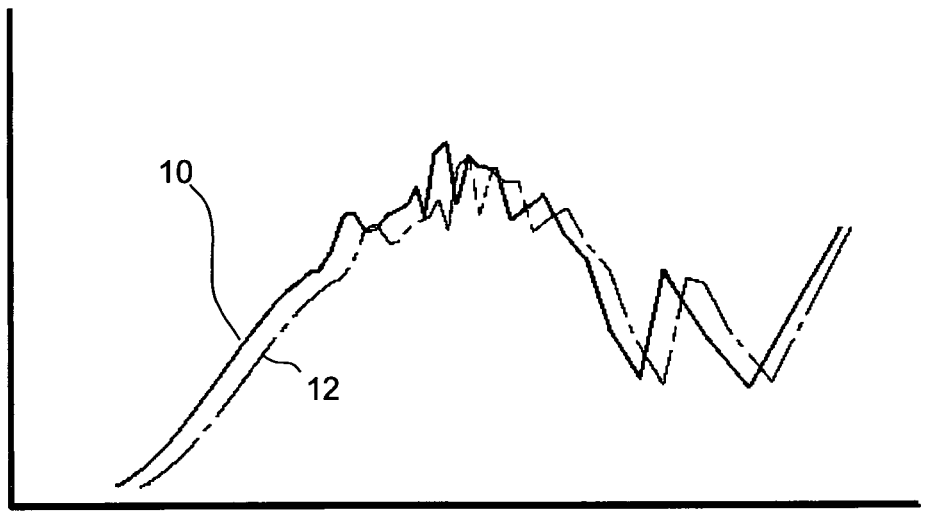
FIGS. 1 and 2 illustrate computed diffusivity distributions of a sample of crude oil and mixtures with drive fluid.
Figure 2:
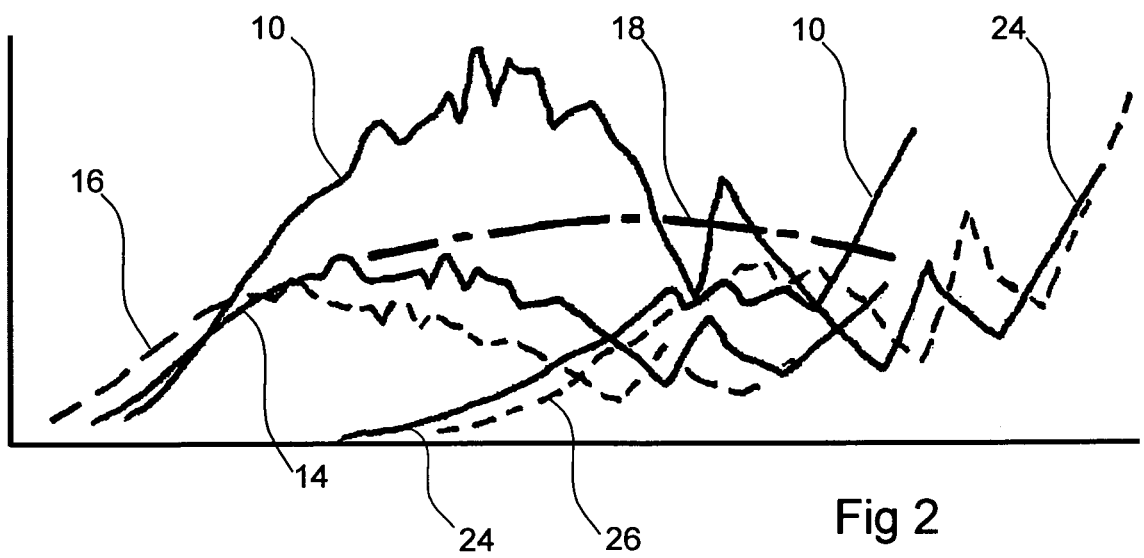

FIGS. 1 and 2 are graphs illustrating diffusivity distributions calculated for reservoir conditions of 100° C. and 500 bar pressure. The horizontal axis is diffusion coefficient, usually shown on a logarithmic scale. The vertical axis is proton signal density within a small increment of the horizontal axis. For present purposes the vertical at any point on the curve can be understood as representing the molar concentration of hydrogen atoms of molecules having the diffusion coefficient which is the horizontal value. The composition of a sample of crude oil was determined by gas chromatography. Curve 10 is the diffusivity distribution calculated from that composition using the formulae which have previously been used for inferring a composition by calculation from diffusivity distribution. See in particular US published application 2004/0253743 mentioned earlier and incorporated by reference. The somewhat zig-zag right hand edge of this calculated curve is the region where diffusion coefficients are highest and individual molecular species can be distinguished. There were differences in the amounts of linear and branched isomers of four and five carbon chain lengths in the crude oil sample.

A proposed drive fluid is a gas mixture which is rich in methane. When this gas mixture and the oil are mixed in a 10:90 weight ratio the Peng-Robinson equation of state (used in the PVTPro program) predicts that the gas dissolves in the oil so that the system is still a single phase. The calculated diffusivity distribution of this single phase mixture is the curve 12 shown as a chain line in FIG. 1, which is plainly similar to the curve 10 but shifted towards the right i.e. towards higher values of diffusion coefficient.

However, if the proportion of gas in the mixture is increased beyond a 20:80 weight ratio the PVTPro program predicts that two phases will form, one of them being an oil phase saturated with the gas but depleted of lighter constituents of the original oil, the other being a fluid phase containing supercritical methane; other constituents of the drive fluid and lighter constituents of the original oil. FIG. 2 shows diffusivity distributions for these two phases as calculated from the predicted compositions of the two phases. The distributions for the diluted oil and drive fluid phases when the overall gas:oil ratio is 40:60 are the curves 14 and 24 respectively. The calculated distributions for the diluted oil and drive fluid phases when the overall gas:oil ratio is 63:37 are curves 16 and 26 shown as broken lines.

The calculated combined diffusivity distribution at the gas:oil ratio of 40:60 is also indicated somewhat schematically as the chain line 18. At the left and right edges, it approximates to the corresponding portions of curves 14 and 16.

It can readily be seen that the curves 14 and 16 have maxima at a lower diffusion coefficient values than the maximum of curve 10. The curves 24 and 26 have maxima at higher diffusion coefficient values than the maximum of curve 10 (and higher than the maximum of curve 12, too). The curve 18 is broader than the other curves mentioned. Thus it can be seen that these various curves are distinguishable from one another. It should also be noted that the curve 16 is displaced to the left, i.e. towards lower diffusion coefficient values, compared to the curve 14.

In the event that carbon dioxide is used as the drive fluid, the calculated curves for distributions of original oil, carbon dioxide-saturated residual oil, and drive fluid saturated with oil components would display shapes similar to those in FIGS. 1 and 2 above. However, because NMR logging uses proton NMR and there are no hydrogen atoms in carbon dioxide, the curve for drive fluid saturated with oil components would be likely to have low amplitude in the vertical direction. It is expected that this will make it even easier to distinguish the presence of two phases.

Figure 3:
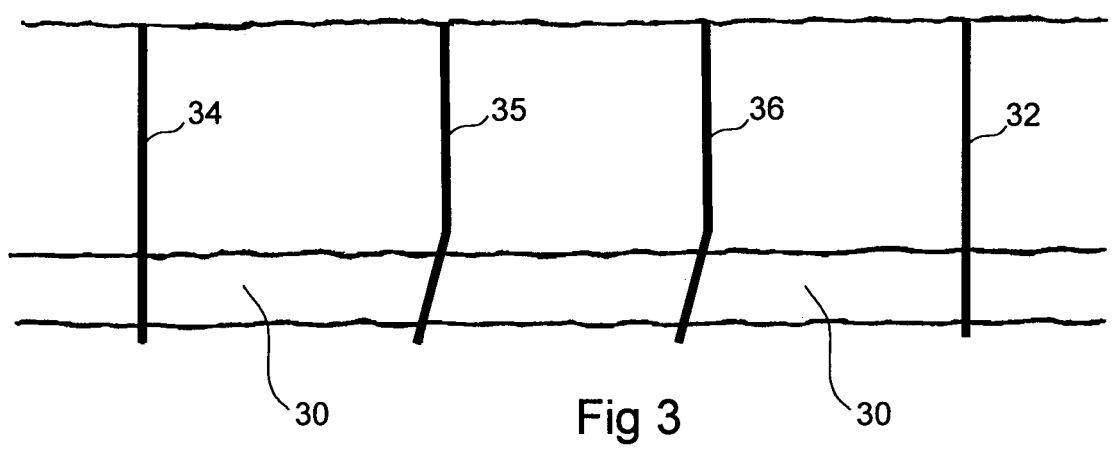
FIG. 3 shows wells accessing parts of a reservoir.

FIG. 3 diagrammatically illustrates a reservoir with wells drilled into it. The reservoir formation itself is indicated as 30. In order to extract oil, there is a production well 32, an injection well 34 and two observation wells 35, 36. The observation wells are cased, but the casing is not perforated so that the interior of each observation wellbore has no path of fluid communication with the reservoir 30.

Figure 4:
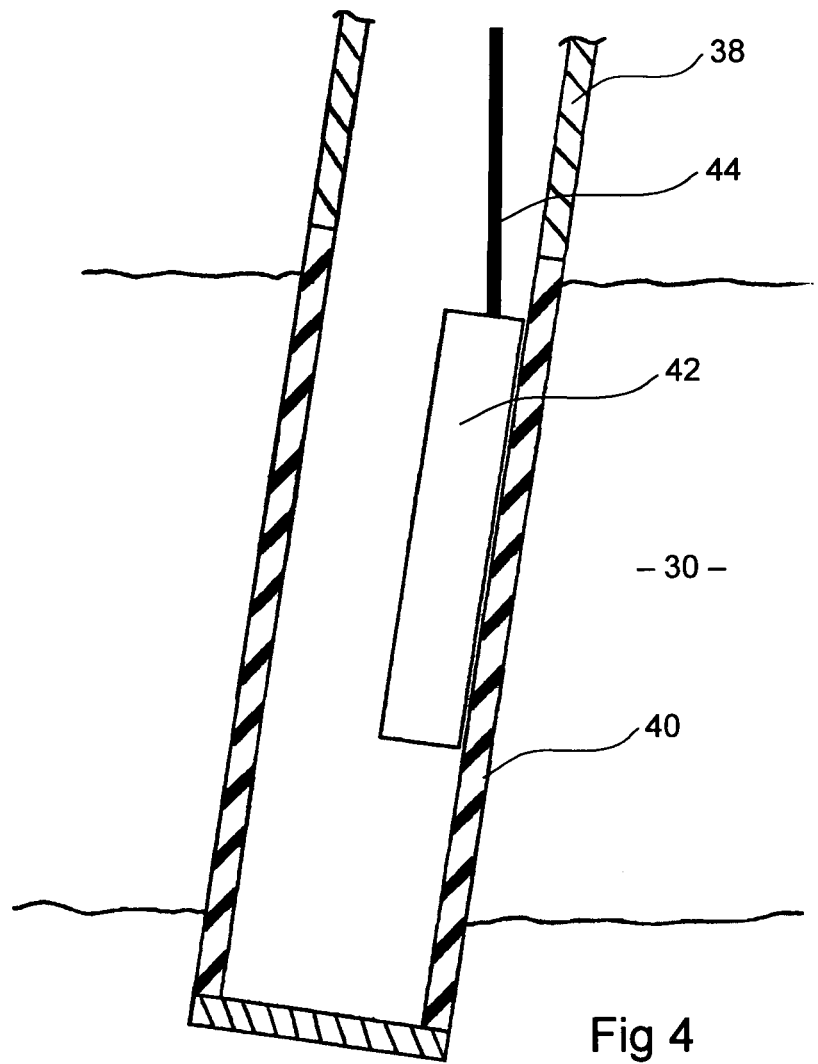
FIG. 4 shows an NMR logging tool in a well.

As shown in FIG. 4, each of the observation wells 35, 36 is deviated to between 5° and 10° to the vertical in the portion penetrating the reservoir 30. Conventional steel casing 38 is used above the reservoir 30 and fibre reinforced plastic casing 40 in the region extending through the reservoir. Fibre reinforced plastic casing is available from several suppliers including Centron International Inc, Mineral Wells, Tex., Composite Pipes Industry LLC, Sohar, Oman, National Oil Varco, Houston, Tex. An NMR logging tool 42 can be lowered into an observation well by means of wireline 44 to perform logging when is desired. This tool 42 will then lie against the fibre reinforced plastic casing 40 and consequently the measurement zone of the tool 42 will lie within the formation 30.

When the first well is drilled into the reservoir formation 30, samples of the original crude oil are collected from the reservoir and sent for laboratory analysis of their composition. Reservoir pressure and temperature are also determined.

It is proposed that miscible displacement will be used to recover oil, injecting gas mixture into the injection well 34 from which it will enter the formation 30 and provide energy to drive oil towards the production well 32. When planning this miscible displacement a drive fluid is chosen, such as locally available natural gas with high methane content. The composition of this gas is also determined by laboratory analysis.

The PVTPro program is used to make predictions concerning mixtures of oil and gas at various weight ratios, all under reservoir temperature and pressure. The program predicts whether each of these mixtures will exist as one or two phases at reservoir temperature and pressure. If two phases are predicted, the program also predicts the composition of each phase. The diffusivity distributions are then calculated for the original oil, each single phase mixture and each phase of each two phase mixture.

The available data on composition, pressure and temperature is used as input to a computer model of the reservoir and used to predict the extent of oil recovery and the composition of the residual oil which is not recovered. Assuming that the predictions are satisfactory, recovery is commenced.

The observation well 35 is NMR logged periodically. After the flood front has passed this well, the diffusivity distribution derived from the NMR data will change noticeably, resembling the broad curve 18 rather than the curve 10. The composition of the mixture behind the flood front can be inferred from the diffusivity distribution. By combining calculated curves for individual phases and fitting the results to the diffusivity distribution obtained by NMR logging, the diffusivity distributions and hence compositions of the individual phases behind the flood front can be inferred. These results can then be compared with compositions predicted computationally, and if appropriate the computer model can be improved to give better consistency with the results obtained and hence a better prediction of the future progress of the oil recovery operation.

Both wells 35 and 36 are now logged periodically to monitor the continuing progress of oil recovery and to detect when the flood front passes well 36. Some time after the flood front has passed the well 35 the composition in the well will consist of a residual oil phase which has been depleted of lighter components and is not changing much more, accompanied by a drive fluid phase moving towards the flood front. The diffusivity distribution of the residual oil can be derived from the observed diffusivity distribution of the mixture (by scaling the diffusivity distribution of the drive fluid and subtracting it from the observed diffusivity distribution) and the composition of the residual oil. If this composition is not as expected the operator may choose to take remedial action, such as making an adjustment to the composition of the drive fluid).

Figure 5:
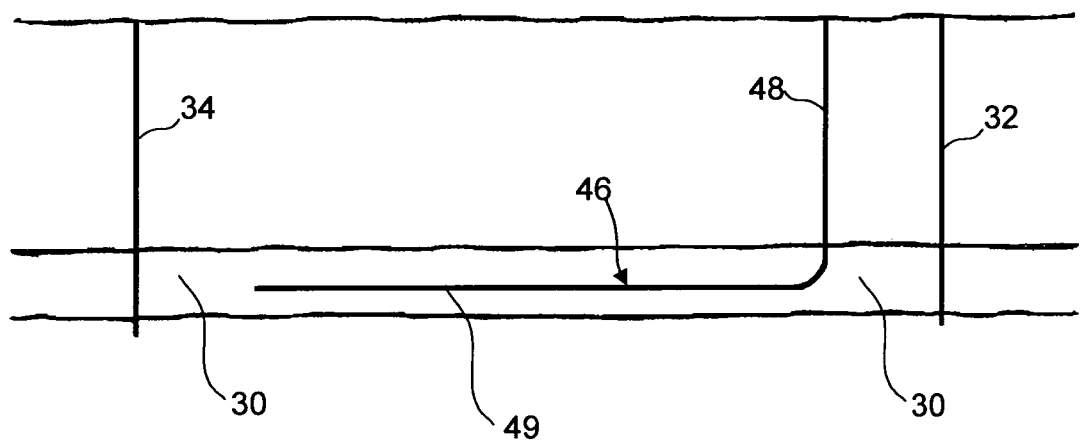
FIG. 5 shows an alternative arrangement of wells accessing parts of a reservoir.

FIG. 5 illustrates an alternative possibility. Instead of multiple observation wells 35,36 there is a highly deviated observation well 46 extending laterally (quite possibly horizontally) within the reservoir. This is cased with conventional steel casing in its portion 48 descending to the reservoir but cased with glass reinforced plastic casing in the region 49 contained within the reservoir formation 30. NMR logging can be carried out along the length of this lateral portion 49, making it possible to locate the current position of the flood front rather than merely waiting for it to pass the wells 35 and 36, and making it possible to obtain diffusivity distributions whenever desired, both for mixtures not far behind the flood front and mixtures a long way behind the flood front.

The invention claimed is:

1. A method of observing composition in a region of an oil reservoir during displacement of oil in the reservoir with a drive fluid which is injected at an injection well to drive oil towards a production well and which is partially miscible with the oil in the reservoir, comprising
   locating an NMR logging tool within a wellbore penetrating the reservoir intermediately between the injection and productions wells so that oil displaced through the reservoir by the drive fluid passes the logging tool
   operating the tool to measure a diffusivity distribution of the composition in the vicinity of the wellbore, and
   deriving properties of composition or phase, or changes in composition or phase of the oil in the vicinity of the wellbore from the measured diffusivity distribution.

2. The method of claim 1 wherein locating an NMR logging tool and operating it to measure a diffusivity distribution is carried out in a plurality of wellbores penetrating the same reservoir intermediately between the injection and production wells.

3. The method of claim 1 wherein locating an NMR logging tool and operating it to measure a diffusivity distribution is carried out repeatedly, at intervals, in the same wellbore.

4. The method of claim 1 wherein locating an NMR logging tool and operating it to measure a diffusivity distribution is carried out repeatedly, at intervals, in each of a plurality of wellbores penetrating the same reservoir intermediately between the injection and production wells.

5. The method of claim 1 wherein the drive fluid contains at least 75% by volume of gas selected from:
   carbon dioxide and
   hydrocarbon which is gaseous under conditions of 25° C. and 1 bar.

6. The method of claim 1 wherein the drive fluid contains at least 50% by volume of hydrocarbon which is gaseous under conditions of 25° C. and 1 bar.

7. The method of claim 1 wherein the drive fluid contains at least 50% by volume carbon dioxide.

8. A method of predicting number of phases and phase composition in an oil reservoir during recovery by miscible displacement of oil in the reservoir with a drive fluid which is injected at an injection well to drive oil towards a production well and which is partially miscible with the oil in the reservoir in accordance with computation from predetermined compositions and values of pressure and temperature, comprising constraining the computation to conform to phase and composition determinations derived from diffusivity distributions obtained by NMR logging with an NMR logging tool located within a wellbore penetrating the reservoir intermediately between the injection and productions wells so that oil displaced through the reservoir by the drive fluid passes the logging tool.

9. A method of recovering oil from a reservoir comprising injecting a drive fluid into the reservoir at an injection well to drive oil through the reservoir to a production well, wherein the drive fluid is partially miscible with the oil in the reservoir,
   providing an NMR logging tool within a wellbore penetrating the reservoir intermediately between the injection and production wells so that oil displaced through the reservoir by the drive fluid passes the logging tool,
   periodically operating the NMR logging tool to measure a diffusivity distribution of the composition in the vicinity of the wellbore containing the logging tool,
   deriving properties of composition or phase, or changes in composition or phase of the oil in the vicinity of the wellbore from the measured diffusivity distribution, and
   continuing to inject drive fluid into the reservoir but selecting rates of injection and/or the composition of injected drive fluid in response to the properties derived from diffusivity distributions obtained by NMR logging.

10. A method of recovering oil from a reservoir comprising injecting a drive fluid into the reservoir at an injection well to drive oil through the reservoir to a production well, wherein the drive fluid is partially miscible with the oil in the reservoir, and observing composition in a region of the reservoir by
   providing an NMR logging tool within a wellbore penetrating the reservoir intermediately between the injection and production wells so that oil displaced through the reservoir by the drive fluid passes the logging tool,
   periodically operating the NMR logging tool to measure a diffusivity distribution of the composition in the vicinity of the wellbore containing the logging tool, and
   deriving properties of composition or phase, or changes in composition or phase of the oil in the vicinity of the wellbore from the measured diffusivity distribution.

11. The method of claim 10 wherein locating an NMR logging tool and operating it to measure a diffusivity distribution is carried out repeatedly, at intervals, in the same wellbore.

12. The method of claim 10 wherein locating an NMR logging tool and operating it to measure a diffusivity distribution is carried out repeatedly, at intervals, in each of a plurality of wellbores penetrating the same reservoir intermediately between the injection and production wells.

13. The method of claim 10 wherein the drive fluid contains at least 75% by volume of gas selected from:
   carbon dioxide and
   hydrocarbon which is gaseous under conditions of 25° C. and 1 bar.

14. The method of claim 10 wherein the drive fluid contains at least 50% by volume of hydrocarbon which is gaseous under conditions of 25° C. and 1 bar.

15. The method of claim 10 wherein the drive fluid contains at least 50% by volume carbon dioxide.

16. The method of claim 1 wherein the wellbore penetrating the reservoir intermediately between the injection and production wells is a cased wellbore comprising a section within the reservoir, in which the casing is non-magnetic.

17. The method of claim 1 wherein the wellbore penetrating the reservoir intermediately between the injection and production wells is a cased observation wellbore which does not have fluid communication with the reservoir.

18. The method of claim 10 wherein the wellbore penetrating the reservoir intermediately between the injection and production wells is a cased wellbore comprising a section within the reservoir, in which the casing is non-magnetic.

19. The method of claim 10 wherein the wellbore penetrating the reservoir intermediately between the injection and production wells is a cased observation wellbore which does not have fluid communication with the reservoir.

\* \* \* \* \*